United States Patent
O'Connor

(10) Patent No.: US 10,882,743 B2
(45) Date of Patent: Jan. 5, 2021

(54) PROCESS FOR THE PRODUCTION OF HYDROGEN

(71) Applicant: CLIMEWORKS AG, Zurich (CH)

(72) Inventor: Paul O'Connor, Hoevelaken (NL)

(73) Assignee: CLIMEWORKS AG, Zurich (CH)

(*) Notice: Subject to any disclaimer, the term of this patent is extended or adjusted under 35 U.S.C. 154(b) by 0 days.

(21) Appl. No.: 16/483,253

(22) PCT Filed: Feb. 2, 2018

(86) PCT No.: PCT/EP2018/052669
§ 371 (c)(1),
(2) Date: Aug. 2, 2019

(87) PCT Pub. No.: WO2018/141911
PCT Pub. Date: Aug. 9, 2018

(65) Prior Publication Data
US 2019/0375633 A1  Dec. 12, 2019

Related U.S. Application Data

(60) Provisional application No. 62/454,834, filed on Feb. 5, 2017.

(51) Int. Cl.
| | | |
|---|---|---|
| *C01B 3/34* | (2006.01) | |
| *C01B 32/15* | (2017.01) | |
| *C01B 3/26* | (2006.01) | |
| *C01B 3/40* | (2006.01) | |
| *C07C 1/12* | (2006.01) | |
| *C07C 29/151* | (2006.01) | |
| *D01F 9/127* | (2006.01) | |

(52) U.S. Cl.
CPC .......... *C01B 3/348* (2013.01); *C01B 3/26* (2013.01); *C01B 3/40* (2013.01); *C01B 32/15* (2017.08); *C07C 1/12* (2013.01); *C07C 29/151* (2013.01); *D01F 9/127* (2013.01); *C01B 2203/0277* (2013.01); *C01B 2203/061* (2013.01); *C01B 2203/062* (2013.01); *C01B 2203/0822* (2013.01); *C01B 2203/0827* (2013.01); *C01B 2203/0855* (2013.01); *C01B 2203/1058* (2013.01); *C01B 2203/1076* (2013.01); *C01B 2203/1082* (2013.01); *C01B 2203/1241* (2013.01)

(58) Field of Classification Search
CPC ..... C01B 3/24; C01B 3/34; C01B 2203/0277; C01B 2203/061; C01B 2203/062; C07C 29/1518; C07C 31/04; C09C 1/54; B01J 10/005
See application file for complete search history.

(56) References Cited

U.S. PATENT DOCUMENTS

| | | | |
|---|---|---|---|
| 2,108,438 A | 2/1938 | Kimball | |
| 2,760,847 A * | 8/1956 | Boedeker | ............... B01J 8/20 |
| | | | 423/453 |
| 3,223,618 A | 12/1965 | Convery et al. | |
| 3,505,018 A | 4/1970 | Bawa et al. | |
| 5,767,165 A | 6/1998 | Steinberg et al. | |
| 2008/0210908 A1* | 9/2008 | Zhu | ............... B82Y 30/00 |
| | | | 252/372 |
| 2014/0331992 A1* | 11/2014 | Tschentscher | ............ C13K 1/02 |
| | | | 127/34 |

FOREIGN PATENT DOCUMENTS

| | | |
|---|---|---|
| DE | 102013112205 A1 | 5/2014 |
| EP | 2620442 A1 | 7/2019 |
| WO | 2015071443 A1 | 5/2015 |
| WO | 2015082567 A1 | 6/2015 |

OTHER PUBLICATIONS

Guodong Zhang, Influence of Molten Salts on Soybean Oil Catalytic Pyrolysis with/without a Basic Catalyst, Energy & Fuels, vol. 28, No. 1, Dec. 13, 2013 (Dec. 13, 2013), pp. 535-541, XP055463561, Washington, DC, US. ISSN: 0887-0624, DOI:10.1021/ef4015845, cited in the OEE work product.

Abanades, et al., Development of methane decarbonisation based on liquid metal technology for $CO_2$-free production of hydrogen, International Journal of Hydrogen Energy, Elsevier Science Publishes B.V. Barking, GB, vol. 41, No. 19, Dec. 23, 2015, pp. 8159-8167.

Shah, et al., Hydrogen Production by Catalytic Decomposition of Methane, Energy & Fuels 2001, 15 (6) pp. 1528-1534.

International Search Report issued in corresponding PCT/EP2018/052669 dated Apr. 23, 2018.

* cited by examiner

*Primary Examiner* — Jafar F Parsa
(74) *Attorney, Agent, or Firm* — Sughrue Mion, PLLC

(57) ABSTRACT

The invention relates to a process to convert hydrocarbons into hydrogen and a separate carbon phase, whereby in step a) the hydrocarbons are contacted with a molten salt, preferably comprising Zinc Chloride, at temperatures preferably above 500° C. and in step b) a solid or liquid carbon phase is separated from the molten salt at a lower temperature, preferably below 150° C. The molten salt is then preferably re-heated to the desired temperature and recycled to step a). The process avoids the emission of $CO_2$, making the hydrogen produced in this way a zero $CO_2$ emission fuel and which also produces a carbon product produced having a use value.

29 Claims, No Drawings

US 10,882,743 B2

PROCESS FOR THE PRODUCTION OF HYDROGEN

CROSS REFERENCE TO RELATED APPLICATIONS

This application is a National Stage of International Application No. PCT/EP2018/052669 filed Feb. 2, 2018, claiming priority based on U.S. Provisional Patent Application No. 62/454,834 filed Feb. 5, 2017.

BACKGROUND OF THE INVENTION

1. Field of the Invention

The invention relates to a process for converting hydrocarbons in a hydrocarbon feed to hydrogen.

2. Description of the Related Art

In the prior art several processes are described to produce hydrogen from hydrocarbons, for example steam reforming, steam cracking, fluid catalytic cracking (FCC) and catalytic cracking of methane over supported nickel catalysts.
Steam Reforming of Hydrocarbons Steam reforming of hydrocarbons is the most feasible route today of producing hydrogen from hydrocarbons. Steam reforming is a method for producing hydrogen, carbon monoxide, or other useful products from hydrocarbon fuels such as natural gas. This is achieved in a processing device called a reformer, which reacts steam at high temperature with the fossil fuel. The steam methane reformer is widely used in industry to make hydrogen. There is also interest in the development of much smaller units based on similar technology to produce hydrogen as a feedstock for fuel cells. Small-scale steam reforming units to supply fuel cells are currently the subject of research and development, typically involving the reforming of methanol, but other fuels are also being considered such as propane, gasoline, auto-gas, diesel fuel, and ethanol. The overall reaction hereby for $CH_4$ gas is: $CH_4+2H_2O \rightarrow 4H_2+CO_2$. Unfortunately, the carbon present in the hydrocarbon is converted into $CO_2$ and, although useful for the production of clean hydrogen gas, this process still has the disadvantage of producing $CO_2$ emissions of fossil fuels.
Steam Cracking, Fluid Catalytic Cracking (FCC)

It is widely known that in a process for the fluid catalytic cracking (FCC process) or steam cracking of high boiling oils to lower boiling hydrocarbons of greater commercial value some hydrogen is also produced However, in these processes the aim is to crack higher produce hydrocarbons to lower hydrocarbons like diesel, gasoline etc. and hydrogen production is an undesired side reaction as it means a loss of higher value hydrocarbons and fouling of the process, so many efforts in this field have been to reduce the amount of hydrogen produced as much as possible.

For example in U.S. Pat. No. 3,223,618 a process is described for the cracking of crude asphalt base crude petroleum, which process comprises a pretreatment of the crude petroleum involving the contacting with Zinc Chloride at temperatures between about 220° C. and 500° C., preferably 250° C. to 450° C. more preferably between 300-400° C. to remove coke formers like Sulphur, nitrogen and metals to produce clean oil to be used as feedstock for a subsequent catalytic cracking step. This process produces a small amount of hydrogen (up to 0.3 wt %) as a side product. U.S. Pat. No. 2,108,438 describes a process for refining of hydrocarbon at a temperature below the zinc chloride fusion temperature and treating the oil in the vapor phase.
Catalytic Cracking of Methane Over Supported Nickel Catalysts In Energy Fuels, 2001, 15 (6), pp 1528-1534 (HYDROGEN PRODUCTION BY CATALYTIC DECOMPOSITION OF METHANE by Naresh Shah, Devadas Panjala and Gerald P. Huffman) it has been suggested that catalytic cracking of methane over supported nickel catalysts is a potential route to the production of CO-free hydrogen and filamentous carbon. Eventually, however, the catalyst deactivates due to the spatial limitations imposed on the filamentous carbon growth by the reactor. The catalyst can be regenerated with steam forming hydrogen and $CO_2$ similar to steam reforming. The continuous regeneration of the catalyst and the separation of the carbon remains a difficult challenge and also this process has the unavoidable disadvantage of producing $CO_2$. Methane cracking has been dogged by problems including carbon clogging and low conversion rates.
Catalytic Cracking of Methane in Catalytic Molten Metals In Journal of hydrogen Energy; Volume 41, Issue 19, 25 May 2016, Pages 8159-8167, and in Science 358, 917-921 (2017), Upham e.a. an alternative approach is described wherein hydrocarbons are contacted with molten metals (e.g. Tin and Nickel/Bismuth mixtures) acting as dehydrogenation catalyst at temperatures between 800° C. and 1200° C. wherein apart form hydrogen a solid and/or liquid carbon phase is formed that can be continuously separated from the liquid molten metals so that these liquid metals catalyst can be reused. Herein, fine methane bubbles are injected at the bottom of a column filled with molten metals. The cracking reaction happens when these bubbles rise to the surface of the liquid metal. carbon separates on the surface of the bubbles and is deposited as a powder at the top end of the reactor when they disintegrate. High-quality carbon can be efficiently produced at temperatures above 800° C. The problem of the molten salt approach is the handling of molten metals at these high temperatures. The carbon phase cannot be separated at temperatures below the melting temperature of the metal. At temperatures above the melting temperatures of the metal the carbon phase cannot be exposed to air without risk of combustion or even explosion and $CO_2$ production. Handling under inert atmosphere is expensive and difficult to realise. Another disadvantage is the high cost of the heat required to sustain these high temperatures (800-1200° C.).

The problem underlying the invention is to provide a process for the production of hydrogen that does not have at least one of the abovementioned disadvantages. In particular, the objective is to provide a process that reduces the $CO_2$ effect/footprint of converting fossil fuels into energy.

SUMMARY OF THE INVENTION

According to the invention there is provided a process to convert hydrocarbons in a hydrocarbon feed into hydrogen and a carbon phase, comprising the following steps:
  a) contacting hydrocarbons with a molten salt at a temperature T1 above 250° C., preferably above 500° C. and preferably below 1000° C. wherein the hydrocarbons are cracked to produce hydrogen,
  b) cooling and separating the solid or liquid carbon phase from the molten salt at a temperature T2 below T1 and below 500° C., preferably below 200° C., 150° C. or even below 100° C., c) preferably followed by re-heating and recycling the molten salt to contacting step a).

The higher the carbon to hydrogen (C/H) ratio of the fuel, the higher the $CO_2$ impact; Hence gas is therefore preferred above oil and oil above coal. The $CO_2$ emitted per energy formed from converting the fuel is the highest for Coal and the lowest for gas. With the process of the invention the $CO_2$ impact of gas and/or oil can be reduced, by extracting hydrogen from these sources without producing and/or emitting $CO_2$.

The process is based on the reaction: hydrocarbon (C, H)→hydrogen ($H_2$)+carbon (C) whereby hydrogen is in the gas phase and carbon in the liquid or solid phase and therefore can be easily separated from each other. A preferred example is methane gas conversion: $CH_4 \rightarrow 2H_2+C$.

In the process the hydrocarbon in a hydrocarbon feed are contacted with a molten salt, which is a harmless water like liquid already at temperatures below 100° C. and which can be heated up to high temperatures without significant loss by sublimation or degradation. Molten salts like $ZnCl_2$, $AlCl_3$ $AlCl_3/SbCl_3$ blends and others also have inherent catalytic activity, which enhances the conversion of hydrocarbons and therefore can be more effective in generating hydrogen at lower temperatures than molten metals like for instance Tin.

The invention thus pertains to a process for producing $CO_2$ friendly hydrogen from Fossil hydrocarbons. Meaning that it becomes possible to produce environmentally friendly (Zero $CO_2$ emissions) hydrogen based on Fossil sources as oil, shale and gas.

As a byproduct a solid and/or liquid carbon phase can be produced suitable for various applications whereby no $CO_2$ is emitted such as: bitumen, carbon black, polymer fillers, carbon based fertilizers, etc. Under certain conditions also a carbon solid can be produced suitable as a carbon Nano Fiber (CNF) or as a precursor for CNF.

In an embodiment of the invention the hydrogen produced can be used to react with $CO_2$ captured from air and/or flue gas to produce a hydrocarbon, preferably methanol. Processes for such conversion are described in detail in WO2015/071443 or in WO 2015/082567 incorporated herein by reference. In this embodiment the ecological footprint is further reduced.

DETAILED DESCRIPTION OF THE INVENTION

The process to convert hydrocarbons in a hydrocarbon feed into hydrogen and a carbon phase, comprises contacting the hydrocarbons in a hydrocarbon feed with a molten salt at a temperature T1 above 250° C. However, higher temperatures are preferred in view of higher conversion to hydrogen and solid carbon, preferably above 350, 500 or even higher then 750° C. In general there is no need to go over 1000° C. The hydrogen escapes from the reaction mixture as gas as the conversion reaction proceeds.

After at least partial, preferably complete conversion of the hydrocarbons, the reaction product is cooled to a temperature T2 below T1 and below 500° C., preferably below 350 or 200° C. At the lower temperature T2 the solid or liquid carbon phase is separated from the molten salt. It is a particular advantage of the use of molten salt that it is possible to go to low temperatures where it is relatively easy to separate the solid or liquid carbon phase. Compared to processes using molten metals there is less risk of auto-combustion in air and no necessity to use inert atmosphere. Therefore it is more preferred that the reaction product is cooled to a temperature 150° C. or even below 100° C.

After separation of the solid or liquid carbon phase the remaining molten salt is preferably re-heating and recycled i.e. preferably to the contacting step.

In the process the molten salt preferably is a metal halide, preferably chosen from the group of $ZnCl_2$, $AlCl_3$, $SbCl_3$, hydrates thereof and blends thereof. A suitable blend is a $AlCl_3/SbCl_3$ blend. Most preferably the molten salt is a $ZnCl_2$ salt, preferably a $ZnCl_2$ hydrate, preferably $ZnCl_2.4H_2O$ in view of the lower melting temperature.

When using a molten salt hydrate, water may evaporate from the molten salt during the conversion at high temperatures, in which case it is preferred to add water during the cooling preferably to about the original amount of water in the molten salt hydrate. Preferably additionally ZnO is added for corrosion resistance. It is noted that materials such as Aluminum chloride and Ferric chloride are not practical because at the very high temperatures because they sublime.

An advantage of the process of the invention is the low melting temperature of the molten salts (even below 100° C.) combined with the catalytic activity thereof, whereby the hydrogen production is enhanced at lower temperatures than in a process using molten metals and whereby the catalytic activity of the molten salts is maintained at a high level by removing the carbon phase formed.

The removing of the carbon phase is preferably done continuously by taking part of the conversion reaction product in a side stream, then cooling the side-stream continuously to T2 and separating the carbon phase from that lower temperature side-stream. After that the side-stream is preferably recycled back to the conversion step.

A further advantage of the process of the invention compared to other processes is that the pressure is not critical and for reasons of convenience atmospheric or ambient pressure is preferred. Reaction times can vary from 10 minutes to 50 hours depending in part on the temperature and on the type and amount of feed.

The hydrocarbon feed can widely chosen but preferably the C/H ratio in the feed is as low as possible in view of optimizing hydrogen production. The hydrocarbon feed can be a mineral oil or biobased material. Most preferred is an oil-based feed, preferably the hydrocarbon is an alkane. In view of hydrogen production methane gas is most preferred. Higher alkanes are more easy to convert but less preferred in view of C/H ratio.

Alternatively the hydrocarbon to be converted is a carbohydrate, preferably from biomass waste feed, for example cellulose. In this case, apart from hydrogen and a carbon phase, also water will be produced, which can be easily separated from the molten salt. Although the production of water means a loss of hydrogen, the process is very useful to convert biomass waste to a hydrogen fuel and other useful products without producing $CO_2$.

The amount of hydrocarbon fed to the molten salt in conversion step a) is between 0.1 and 50, preferably 1-40, 30, 20 wt % and the amount of molten salt is between 0.1 and 50, preferably 1-60, 70, 80 wt % relative to the total weight of the molten salt and hydrocarbon.

It is preferred to add a solid carbon source or a precursor thereof in step a) and/or b) as a seed to enhance the separation of the carbon phase from the molten salt phase. The speed of formation and separation of the carbon phase can be enhanced by adding a "seeding" carbon phase material during the reaction and/or separation step. It is believed that the solid carbon catalyses the conversion reaction and may nucleate the formation and growth of the carbon phase. Preferably the amount of solid carbon source or a precursor thereof is between 0.1 and 10 wt %, preferably between 0.1 and 5 or 3 wt % relative to the total weight of the molten salt and the hydrocarbon. Examples of a solid carbon source is charcoal, carbon black, carbon fibers, carbon nano-fibers etc A solid carbon source precursor is a compound that in the molten salt is directly converted to a solid carbon source, for example a cellulose or lignin.

In the process the molten salt further preferably comprises one or more dehydrogenation catalyst metals preferably chosen from the group of Ni, Fe, Zn or Cu, to enhance hydrogen yield in the process. The catalytic metals is chosen different from the metal of the molten salt. This is particularly preferred at lower conversion temperatures (400-800° C.).

The metals can be added in the form of a metal-organic complex like metal-alkyls, metal-oxides or a metal-chloride complex and preferably in an amount of less than 10, preferably less than 5 or even less than 3 mole % of the metal in the molten salt. In the molten salt the metals are present as metal ions. The metal ions can be added in metallic form as they can convert to metal ions at high temperature in the molten salt. Most preferred is using Zink chloride molten salt with Ni or Fe metals as dehydrogenation catalyst metals. In a preferred embodiment Iron (Fe) is included as active metal enabling a magnetic separation of the active metal catalyst from the carbon produced.

In a useful embodiment the dehydrogenation catalyst metals are supported on a solid carbon source or precursor thereof. The solid carbon source or precursor thereof for use as seed in the separation or as support for the catalyst metal are same or different compound selected from carbon fiber, lignin, cellulosic fiber, carbon nanofiber or carbon nanotube.

In view of the $CO_2$ emission reduction it is preferred that the energy required in the process is produced by the combustion of hydrogen produced in the process and/or produced from renewable sources, for example solar, wind or hydro-electrical sources. The energy required in the process for heating and conversion is preferably added via electro-magnetic waves, such as microwaves. This will result at a better conversion at lower temperatures.

It is a particular advantage of the process that the separation can more easily and more completely be done at such low temperatures as indicated; most preferably between 50 and 150° C. The separation already takes place as a result of cooling to lower temperature, but can be accelerated or improved in ways known in the art. Preferably in step b) an anti-solvent is added to promote the precipitation/agglomeration of the carbon and facilitate separation from between the molten salt phase and the carbon phase. Suitable anti-solvents for separation from molten salts after cooling are described in EP2620442, and are preferably organic compounds such as but not limited to ketones, alcohols, ethers, alkanenitriles, for example acetone, ether, methanol or ethanol. In a particular embodiment the separation between the molten salt and the carbon phase is performed by adding solvent, coagulant or anti-solvent before-, during or after extrusion and/or spinning of the converted reaction product to facilitate the separation from the molten salt whilst forming carbon extrudate or fibers.

It is a particular advantage of the process that the solid or liquid carbon stream separated from the molten salt can produce or can be used to produce valuable higher quality carbon materials. Preferably, the carbon phase produced comprises Carbon Nano Fiber (CNF) or a CNF precursor. The formation of these desirable products can be stimulated by seeding with the same products. The formed products after isolation can be used as seed in the same process. The formation of these desirable products can further be stimulated by choosing higher conversion temperatures, preferably above 500° C., more preferably above 800° C.

The process may further comprising one or more further process steps wherein the obtained carbon phase is used to produce one or more products selected from carbon sol fertilizer, carbon black, carbon fibers, carbon nano-fibers or precursors thereof. In a special embodiment the formation of hydrogen in step a) is performed at high temperatures as specified above but below 800° C., and the separated carbon phase produced in step b) is further processed in a separate step at temperatures above 800° C. to enhance the formation of higher quality carbon materials.

In a special embodiment of the process according to the invention the process further comprising a process step wherein the hydrogen produced is reacted with $CO_2$ captured from air and/or flue gas to produce a hydrocarbon, preferably methanol.

What is claimed is:

1. A process to convert hydrocarbons in a hydrocarbon feed into hydrogen and a carbon phase, comprising the following steps:
   a) contacting hydrocarbons with a molten salt at a temperature T1 above 250° C., wherein the hydrocarbons are cracked to produce hydrogen, and
   b) cooling and separating the solid or liquid carbon phase from the molten salt at a temperature T2 below T1 and below 500° C.,
   wherein the amount of hydrocarbon added in step a) is between 0.1 and 50 and the amount of molten salt is between 0.1 and 50 relative to the total weight of the molten salt and hydrocarbon.

2. The process according to claim 1, wherein the molten salt is a metal halide.

3. The process according to claim 2, wherein the hydrocarbon to be converted is oil-based or wherein the hydrocarbon to be converted is a carbohydrate.

4. A process to convert hydrocarbons in a hydrocarbon feed into hydrogen and a carbon phase, comprising the following steps:
   a) contacting hydrocarbons with a molten salt at a temperature T1 above 250° C., wherein the hydrocarbons are cracked to produce hydrogen,
   b) cooling and separating the solid or liquid carbon phase from the molten salt at a temperature T2 below T1 and below 500° C., and
   c) followed by re-heating and recycling the molten salt to contacting step a),
   wherein a solid carbon source or a precursor thereof is added in step a) and/or b) as a seed to enhance the separation of the carbon phase from the molten salt phase.

5. The process according to claim 1, wherein the molten salt further comprises one or more dehydrogenation catalyst metals different from the metal in the molten salt, to enhance hydrogen yield in the process.

6. The process according to claim 5, wherein the dehydrogenation catalyst metals are supported on a solid carbon source or precursor thereof.

7. The process according to claim 1, wherein solid carbon source or precursor thereof for use as seed in the separation or as support for the catalyst metal are same or different compound selected from the group consisting of carbon fiber, lignin, cellulosic fiber, carbon nanofiber or carbon nanotube.

8. The process according to claim 1, wherein energy required in the process is produced by the combustion of hydrogen produced in the process and/or produced from renewable sources.

9. The process according to claim 1, wherein the energy required in the process for heating and conversion is added via electro-magnetic waves, including microwaves.

10. The process according to claim 1, wherein in step b) an anti-solvent is added to improve the separation between the molten salt phase and the carbon phase.

11. The process according to claim 1, wherein the separation between the molten salt and the carbon phase is performed by extrusion and/or spinning adding a solvent, coagulant or anti-solvent to facilitate the separation.

12. The process according to claim 1, wherein the carbon phase produced comprises carbon Nano Fiber (CNF) or a CNF precursor.

13. The process according to claim 1, wherein the formation of hydrogen in step a) is performed at temperatures below 800° C., and wherein the separated carbon phase produced in step b) is further processed in a separate step at temperatures above 800° C. to enhance the formation of higher quality carbon materials.

14. A process to convert hydrocarbons in a hydrocarbon feed into hydrogen and a carbon phase, comprising the following steps:
a) contacting hydrocarbons with a molten salt at a temperature T1 above 250° C. wherein the hydrocarbons are cracked to produce hydrogen, and
b) cooling and separating the solid or liquid carbon phase from the molten salt at a temperature T2 below T1 and below 500° C.,
wherein the amount of hydrocarbon added in step a) is between 0.1 and 50 and the amount of molten salt is between 0.1 and 50 relative to the total weight of the molten salt and hydrocarbon,
further comprising a process step wherein the hydrogen produced is reacted with $CO_2$ captured from air and/or flue gas to produce a hydrocarbon.

15. The process according to claim 1, further comprising one or more process steps wherein the obtained carbon phase is used to produce one or more products selected from the group consisting of carbon sol fertilizer, carbon black, carbon fibers, carbon nano-fibers or precursors thereof.

16. The process according to claim 1, wherein the molten salt is a metal halide, selected from the group consisting of $ZnCl_2$, $AlCl_3$, $SbCl_3$, hydrates thereof and blends thereof.

17. The process according to claim 1, wherein the molten salt is a metal halide, selected from the group consisting of $AlCl_3/SbCl_3$ blend, $ZnCl_2$, $ZnCl_2$ hydrate.

18. The process according to claim 1, wherein the molten salt is $ZnCl_2$ or $ZnCl_2.4H_2O$ and which additionally comprises $ZnO$.

19. The process according to claim 1, wherein the hydrocarbon to be converted is oil-based alkane, including methane, or wherein the hydrocarbon to be converted is a carbohydrate, from biomass waste feed.

20. The process according to claim 1, wherein in step a) hydrocarbons are contacted with a molten salt at a temperature T1 above 500° C. and/or below 1000° C. wherein the hydrocarbons are cracked to produce hydrogen.

21. The process according to claim 1, wherein step b) involves cooling and separating the solid or liquid carbon phase from the molten salt at a temperature T2 below T1 and below 200° C., or below 150° C. or even below 100° C.

22. The process according to claim 1, wherein step b) is followed by c) by re-heating and recycling the molten salt to contacting step a).

23. The process according to claim 1, wherein the amount of hydrocarbon added in step a) is between 1-40 wt % and the amount of molten salt is between 1-60 wt % relative to the total weight of the molten salt and hydrocarbon.

24. The process according to claim 1, wherein the molten salt further comprises one or more dehydrogenation catalyst metals different from the metal in the molten salt, chosen from the group of Ni, Fe, Zn or Cu, to enhance hydrogen yield in the process, and preferably in an amount of less than 10 mole % of the metal in the molten salt.

25. The process according to claim 1, further comprising a process step wherein the hydrogen produced is reacted with $CO_2$ captured from air and/or flue gas to produce a methanol.

26. The process according to claim 4, wherein the amount of solid carbon source or a precursor thereof is between 0.1 and 10 wt %, or between 0.1 and 5 or 3 wt % relative to the total weight of the molten salt and the hydrocarbon.

27. The process according to claim 4, wherein in step a) hydrocarbons are contacted with a molten salt at a temperature T1 above 500° C. and/or below 1000° C. wherein the hydrocarbons are cracked to produce hydrogen.

28. The process according to claim 4, wherein step b) involves cooling and separating the solid or liquid carbon phase from the molten salt at a temperature T2 below T1 and below 200° C., or below 150° C. or even below 100° C.

29. The process according to claim 4, wherein step b) is followed by c) by re-heating and recycling the molten salt to contacting step a).

* * * * *